United States Patent [19]

Shafer et al.

[11] Patent Number: 5,284,818
[45] Date of Patent: Feb. 8, 1994

[54] FORMULATIONS AND PROCESS FOR EXTENDING THE VASE LIFE OF CUT FLOWERS

[75] Inventors: Warren E. Shafer, Libertyville; Derek D. Woolard, Waukegan; Neyyan K. P. Samuel, Vernon Hills; Gregory D. Venburg, Deerfield; Balan N. Devisetty, Buffalo Grove; Daniel F. Heiman, Libertyville, all of Ill.

[73] Assignee: Abbott Laboratories, Abbott Park, Ill.

[21] Appl. No.: 26,920

[22] Filed: Mar. 8, 1993

Related U.S. Application Data

[63] Continuation-in-part of Ser. No. 780,657, Oct. 18, 1991, abandoned.

[51] Int. Cl.$^5$ .............................. A01N 3/02
[52] U.S. Cl. .................................. 504/115
[58] Field of Search ................... 504/114, 115

[56] References Cited

U.S. PATENT DOCUMENTS

| | | | |
|---|---|---|---|
| 3,104,968 | 9/1963 | Fisher | 71/68 |
| 3,122,432 | 2/1964 | Biggs | 71/68 |
| 3,134,661 | 5/1964 | Sheppard | 71/68 |
| 3,239,328 | 3/1966 | Sheppard | 71/68 |
| 3,320,046 | 11/1966 | Siegel | 71/68 |
| 3,328,157 | 6/1967 | Darpinian | 71/68 |
| 3,449,108 | 6/1969 | McConnell et al. | 71/68 |
| 3,751,459 | 8/1973 | Berger et al. | 562/564 |
| 3,775,255 | 11/1973 | Berger et al. | 435/106 |
| 3,826,639 | 7/1974 | Pommer et al. | 71/68 |
| 3,865,569 | 2/1975 | Parups et al. | 71/68 |
| 3,874,871 | 4/1975 | Sy et al. | 71/68 |
| 3,907,539 | 9/1975 | Holdt et al. | 71/68 |
| 3,929,447 | 12/1975 | Beyer et al. | 71/68 |
| 3,929,448 | 12/1975 | Brantley | 71/68 |
| 4,061,490 | 12/1977 | Yukinaga et al. | 71/68 |
| 4,225,679 | 9/1980 | Pilato | 521/109 |
| 4,441,918 | 4/1984 | Rehberg | 71/113 |
| 4,744,811 | 5/1988 | Schulz et al. | 71/68 |
| 4,802,905 | 2/1989 | Spector | 71/68 |
| 5,021,186 | 6/1991 | Ota et al. | 252/186.35 |

FOREIGN PATENT DOCUMENTS 1240173 8/1988 Canada.

OTHER PUBLICATIONS

J. DiMartino, "Preservatives Can Make a Difference" Florist Mazazine, Mar., 1986.
G. Spikman, Sci, Hortic (Amsterdam) 39(1):73–81 1989.
Lee, J. S. et al., Hon'yuk Wonye Hakhoechi (Korean) 31(3):284–293 1989.
C. Y. Yang, et al. HortScience 14(1):59–60 1979.
C. Y. Yang, et al. HortScience 15(3):238–243 1980.
C. Y. Yang, et al. HortScience 15(6):805–806 1980.
"Hormonal Regulations of Development-Molecular Aspects of Plant Hormones" J. MacMillan, Ed., Springer-Verlag, New York, 1980 pp. 317–336.

*Primary Examiner*—Richard L. Raymond
*Assistant Examiner*—Brian Bembenick
*Attorney, Agent, or Firm*—Jerry F. Janssen

[57] ABSTRACT

Stable, solid cut flower preservatives having excellent shelf life and stability comprise from about 1 part by weight to about 99 parts by weight of a sugar, glycoside or mixture thereof, from about 0.05 part by weight to about 2 part by weight of an ACC synthase inhibitor selected from L-trans-2-amino-4-(2-aminoethoxy)-3-butenoic acid and carboxymethoxylamine, from about 0.5 part by weight to about 8 parts by weight of aluminum sulfate having less than about 27 percent by weight water of hydration, and from about 0.05 part by weight to about 5 parts by weight of an antimicrobial agent.

8 Claims, No Drawings

FORMULATIONS AND PROCESS FOR EXTENDING THE VASE LIFE OF CUT FLOWERS

CROSS-REFERENCE TO RELATED APPLICATIONS

This application is a continuation-in-part of copending application Ser. No. 07/780,657 filed Oct. 18, 1991 (abandoned).

TECHNICAL FIELD

This application relates to formulations and a method for prolonging the vase life of cut ornamental flowers. More particularly, the present invention concerns solid cut flower preservative formulations which have good shelf life and which can be readily dissolved in water to provide solutions for prolonging the vase life of cut flowers.

BACKGROUND OF THE INVENTION

The marketing of cut flowers and ornamental flowering plants is of considerable economic importance to the horticultural industry. In 1989, for example, the wholesale United States market for cut flowers and flowering, foliage, and bedding plants amounted to approximately 2.43 billion dollars. The sale of cut flowers contributed approximately 459 million dollars to this total, with the sale of potted flowering plants contributing approximately 522 million dollars.

Cut flowers are subjected to considerable stress during harvesting, handling and shipping, and their vase life, once in the hands of the ultimate consumer, can be considerably shortened as a result. It has been known for some time that plants produce ethylene, particularly in response to stress, by converting methionine into 1-aminocyclopropane-1-carboxylic acid (also known by the acronym "ACC") which is then further converted into ethylene. The plant enzyme responsible for the production of ACC is ACC synthase. Ethylene, a gaseous phytohormone, is believed to be involved in the modulation of a number of plant biochemical pathways affecting such processes as abscission, senescence, flowering, fruit setting, fruit ripening, seed germination, sex expression, root growth, internode elongation, epinasty, and geotropism.

Based upon this understanding of the mechanism of wilting or senescence in cut flowers, various formulations have been suggested in the prior art for preserving the vase life of cut flowers by incorporating agents known to block the activity of ACC synthase. Among cut flower preservative agents which have been suggested in the prior art are L-trans-2-amino-4-(2-aminoethoxy)-3-butenoic acid (also known by the common name "aminoethoxyvinyl glycine" and the acronym "AVG"), and carboxymethoxylamine (also known by the common name "aminooxyacetic acid" and the acronym "AOAA"). J. E. Baker, et al., Hort. Science, 12(1): 38–39 (1977) have reported, for example, that immersing the stems of cut carnations (*Dianthus caryophyllus, L.*) in solutions containing AVG, either alone or in combination with free-radical scavengers such as sodium benzoate or propyl gallate, extended the vase life of the cut flowers. Similar effects on extension of the vase life of cut flowers following treatment with solutions containing AVG have been shown for snapdragons (R. E. Hardenburg, et al., J. Am. Hort. Soc., 102: 517–520 (1977)) and for irises, daffodils, and chrysanthemums (C. Y. Wang, et al., Hort. Science, 14: 59–60 (1979)). Canadian patent 1,240,173 to Gladon teaches a method of preserving cut flowers by immersing the stems in a solution containing AOAA.

Cut flower preservative formulations taught in the prior art include a sugar which provides an energy source for the cut flowers, an antimicrobial agent (believed to prevent clogging by microbial growth of the vascular system of the cut flowers), and inorganic salts. A review of the common ingredients of cut flowers preservative formulations is provided by A. H. Halevy, et al., Horticultural Reviews, 3: 59–143 (1981).

While the method of preserving cut flowers by immersing cut flower stems in solutions containing an ACC synthase inhibitor such as AVG or AOAA is generally known, the prior art has not addressed the problem of how to prepare dry, solid formulations which contain these agents and which have the requisite stability to permit their preparation and storage for extended periods prior to use. Solid formulations containing AVG or AOAA together with an acidic inorganic salt and a sugar, intended for later use in preparing cut flower preservative solutions, tend to lose their effectiveness over time. There is thus a need for solid cut flower preservative formulations containing AVG or AOAA which have the requisite stability to permit pre-packaging and storage for extended periods prior to their use.

SUMMARY OF THE INVENTION

The present invention provides a stable, solid formulation having a long shelf life and which is useful in making up aqueous cut flower preservative solutions.

More particularly the present invention provides, in its principle embodiment, a stable solid cut flower preservative formulation comprising (a) from about 1 part by weight to about 99 parts by weight of a sugar, glycoside or mixture thereof, (b) from about 0.05 part by weight to about 2 part by weight of an ACC synthase inhibitor selected from L-trans-2-amino-4-(2-aminoethoxy)-3-butenoic acid and carboxymethoxylamine, (c) from about 0.5 part by weight to about 8 parts by weight of aluminum sulfate having less than about 27 percent by weight water of hydration, and (d) from about 0.1 part by weight to about 5 parts by weight of an antimicrobial agent.

In another embodiment, the formulations of this invention further comprise from about 0.1 part by weight to about 5 parts by weight sodium or potassium chloride, from about 0.01 parts by weight to about 2 parts by weight of a nonionic and/or anionic surfactant.

DETAILED DESCRIPTION

The formulation of the present invention comprises a dry, powdered mixture of a sugar, glycoside or mixture thereof, an ACC synthase inhibitor selected from L-trans-2-amino-4-(2-aminoethoxy)-3-butenoic acid (AVG) and carboxymethoxylamine (AOAA), aluminum sulfate, an antimicrobial agent and, optionally, other inorganic salts and a nonionic or anionic surfactant. The sugar comprises from about 1 part by weight to about 99 parts by weight of the formulation, preferably from about 80 parts by weight to about 99 parts by weight. Suitable sugars for use in preparing the formulations of this invention are selected from aldopentoses such as ribose, arabinose, xylose and lxyose, aldohexoses such as allose, altrose, glucose, mannose, gulose, idose, galactose, and talose, ketohexoses such as fructose, monosaccharide derivatives such as alkyl-α-, alkyl-β-, aryl-α-, and aryl-β-glycosides such as methyl-α-D-glucopyranoside and phenyl-α-D-glucopyranoside, and salicin, disaccharides such as lactose, maltose, cellobiose, gentiobiose, turanose, isomaltose, laminaribose, melibiose, sucrose and trehalose, and trisaccharides such as raffinose and gentianose. The preferred sugar component of the compositions of this invention is sucrose. The various named sugars are commercially available, for example, from Sigma Chemical Co., St. Louis, Mo. 63178.

The formulations contain, as the primary active ingredient, an ACC synthase inhibitor selected from L-trans-2-amino-4-(2-aminoethoxy)-3-butenoic acid (AVG) and carboxy-methoxylamine (AOAA). The ACC synthase inhibitor content of the dry formulations ranges from about 0.05 part by weight to about 2 part by weight of the inhibitor, preferably about 0.2 to 1 parts by weight. The preferred ACC synthase inhibitor of the compositions of this invention is AVG.

The formulations of this invention further comprise from about 0.5 part by weight to about 8 parts by weight, preferably between about 1 part by weight and about 5 parts by weight, of aluminum sulfate which contains less than about 27 percent by weight of water of hydration. Commercially available hydrated aluminum sulfate contains between about 14 and 18 moles of water of hydration per mole of aluminum sulfate. That is, the commercially available hydrated material corresponds to a formula of $Al_2(SO_4)_3 \cdot xH_2O$ where x may range between about 14 and 18. This material contains 42 percent by weight or greater water of hydration. It has been found that solid formulations containing AVG or AOAA prepared with commercially available hydrated aluminum sulfate are unstable, and subject to decomposition of the AVG or AOAA component. On the other hand, solid formulations prepared in accordance with the present invention containing aluminum sulfate which has been partially dried to a constant weight at a temperature of 100° C.–250° C., preferably at about 105°–120° C. for a period of from 18–36 hours, preferably about 19–22 hours, results in a stable product. The partially dried aluminum sulfate resulting from drying to constant weight at 100°–250° C. may contain about 27 weight percent water of hydration or less, corresponding to material containing about seven moles of water, or less, per mole of aluminum sulfate. The partially dried aluminum sulfate resulting from drying to constant weight at 105°–120° C. preferably contains from 21–24 weight percent of water of hydration, corresponding roughly to the penta- or hexahydrate.

The formulations of the present invention also comprise between about 0.05 part by weight to about 5 parts by weight, preferably about 0.2 parts by weight to about 2 parts by weight, of an antimicrobial agent. Suitable antimicrobial agents for use in the formulations of this invention include 8-hydroxyquinoline or salts thereof (including the citrate, sulfate, or benzoate), chloramphenicol, spectinomycin, alkyl parabens such as methyl or propyl paraben or mixtures of alkyl parabens, salicylic or benzoic acid and their sodium, potassium or ammonium salts, thiabendazole, slow-release chlorine-containing compounds such as 1,3-dichloro-5,5-dimethylhydantoin, and alkali metal sorbate salts, especially potassium sorbate. The preferred antimicrobial agent is 8-hydroxyquinoline citrate.

An anionic or nonionic surfactant, present in an amount of between about 0.01 parts by weight to about 2 parts by weight, preferably between about 0.05 parts by weight and 0.5 parts by weight, and sodium or potassium chloride in an amount ranging between about 0.1 part by weight to about 5 parts by weight, preferably between about 0.1 parts by weight and 1 part by weight, may also be added to the formulations. Suitable nonionic surfactant materials useful for the purposes of this invention include, but are not necessarily limited to, nonionic surfactants such as hexitol anhydrides (hexitans and hexides) derived from sorbitol partially esterified with common fatty acids (e.g. palmitic, stearic and oleic acids). These materials are commercially available under the tradename Span® from The Pierce Chemical Co., P.O. Box 117, Rockford, Ill. 61105. Other suitable nonionic surfactants include materials derived from surfactants of the Span® type by etherification of the free hydroxyl groups with poly(oxyethylene) groups. This latter class of surfactants is available under the tradename Tween® (ICI Americas, Wilmington, Del.). Additionally, polyethoxylated octyl- or nonylphenols (commercially marketed under the tradename Triton®) can also be used. Nonionic surfactants comprising ethoxylated straight chain alcohols, marketed under the tradename Plurafac® by BASF Chemicals, Wyandotte, Mich., as well as nonionic surfactants comprising block copolymers of propylene oxide and ethylene oxide, marketed under the tradenames Pluronic® and Poloxamer® (BASF) can also be used. Additionally, nonionic surfactants which are block polymers of polyoxyalkylene derivatives of ethylenediamine, marketed under the tradename Tetronic® surfactants (BASF) may also be used. Preferred nonionic surfactants in the formulations of the present invention are surfactants of the Pluronic® or Poloxamer® type, particularly Pluronic® F-68 or Poloxamer® 188. Suitable anionic surfactants include alkali metals salts of esters of sulfosuccinic acid such as sodium dioctyl sulfosuccinate, marketed under the tradename Aerosol OT® (American Cyanamid, Wayne, N.J.).

In general, the formulations of the present invention are prepared as dry, powdered mixtures which are stored and shipped as such and dissolved in water immediately prior to use as cut flower preservative solutions. When in the form of dry powders, the formulations of this invention are packaged in bulk for end use, as in containers having a tightly-fitting lid such as screw-capped or snap-capped bottles or, preferably are packaged in plastic or foil packets containing the required amount of material for a single use.

The formulations of the present invention are dissolved in water just prior to use at a concentration ranging between about 5 g/liter to about 30 g/liter, preferably about 7 g/liter to 20 g/liter. For a typical arrangement of cut flowers, the volume of water in a vase is about one-half to one liter. Thus a preferred package of the dry formulations of the present invention is a foil or plastic packet containing about 2.5–30 grams of material.

The dry solid formulations of this invention are prepared generally by first screening the materials through a 100 mesh screen and then blending and milling, under dry conditions, the screened components. Typically, during the formulation about ten percent of the sugar to be used in the final formulation is blended with the other components, with the balance of the sugar added at a final stage, followed by milling and further blending and packaging.

The shelf life stability of the formulations made in accordance with this invention was tested in a series of experiments. Formulations were prepared containing aluminum sulfate both with and without prior drying to constant weight at 110° C. The AVG content of each of the formulations was determined by high performance liquid chromatography techniques immediately after compounding and again after storage at 50° C. for varying periods of time. Storage at 50° C. is typically used in the formulation arts as an accelerated method of estimating shelf life stability of chemical formulations: one month storage at 50° C. is generally held to simulate storage at room temperature for a period of about 1 year. The data from these tests are presented in Table 1.

TABLE 1

Dry Formulation Stability Tests

| Time | Weight Percent AVG Present in Formulation | |
|---|---|---|
| | Partially Dried $Al_2(SO_4)_3$ | Commercial Hydrated $Al_2(SO_4)_3 \cdot 14\text{-}18H_2O$ |
| Initially | 0.34 | 0.36 |
| After 1 week at 50° C. | 0.32 | 0.22 |
| After 2 weeks at 50° C. | 0.32 | 0.14 |
| After 1 month at 50° C. | 0.33 | 0.05 |

As can be seen from the data presented in Table 1, at 50° C. about 39% of the AVG initially present in the formulations containing commercially available hydrated aluminum sulfate was destroyed after only one week (i.e. the AVG content of the formulations dropped from 0.36 weight percent initially to 0.22 weight percent after one week). Correspondingly, after two weeks under these conditions 61% of the AVG had been lost and after one month, 86%. The latter data corresponds to roughly 86% loss of the AVG content of the dry, solid formulation upon storage at room temperature for a period of one year.

On the other hand, for the formulations made in accordance with the teachings of the present invention containing partially dried aluminum sulfate, less than 3% of the AVG initially present in the formulation had been lost under test conditions simulating one year storage at room temperature.

FORMULATION EXAMPLES

EXAMPLE 1

A dry cut flower preservative formulation was prepared by blending the following ingredients to make 100 parts by weight:

| | |
|---|---|
| L-trans-2-amino-4-(2-aminoethoxy)-3-butenoic acid (AVG) | 0.359 parts |
| Sucrose | 97.641 parts |
| Sodium chloride | 0.15 parts |
| 8-Hydroxyquinoline citrate | 0.25 parts |
| Poloxamer ® 188 surfactant | 0.10 parts |
| Aluminum sulfate, dried to constant weight at 110° C. | 1.5 parts |

EXAMPLE 2

| | |
|---|---|
| L-trans-2-amino-4-(2-aminoethoxy)-3-butenoic acid (AVG) | 0.718 parts |
| Sucrose | 95.282 parts |
| Sodium chloride | 0.3 parts |
| 8-Hydroxyquinoline citrate | 0.5 parts |
| Poloxamer ® 188 surfactant | 0.2 parts |
| Aluminum sulfate, dried to constant weight at 110° C. | 3.0 parts |

EXAMPLE 3

(Prior Art)

A composition lacking an ACC synthase inhibitor was prepared in accordance with the teachings of the prior arts by blending the following dry ingredients:

| | |
|---|---|
| Glucose | 95.0 parts by weight |
| 8-Hydroxyquinoline citrate | 0.5 parts by weight |
| Aluminum sulfate (Commercial hydrated form) | 4.0 parts by weight |
| Sodium chloride | 0.3 parts by weight |
| Poloxamer ® 188 | 0.20 parts by weight |

EXAMPLE 4

A composition was prepared by blending the following dry ingredients:

| | |
|---|---|
| Glucose | 94.42 parts by weight |
| AVG | 0.58 parts by weight |
| 8-Hydroxyquinoline citrate | 0.5 parts by weight |
| Aluminum sulfate (Commercial hydrated form) | 4.0 parts by weight |
| Sodium chloride | 0.3 parts by weight |
| Poloxamer ® 188 | 0.2 parts by weight |

EXAMPLE 5

A composition was prepared by blending the following dry ingredients:

| | |
|---|---|
| Glucose | 94.5 parts by weight |
| AOAA | 0.5 parts by weight |
| 8-Hydroxyquinoline citrate | 0.5 parts by weight |
| Aluminum sulfate (Commercial hydrated form) | 4.0 parts by weight |
| Sodium chloride | 0.3 parts by weight |
| Polaxamer ® 188 | 0.2 parts by weight |

EFFICACY STUDIES

The effectiveness of formulations made in accordance with the teachings of the present invention in preserving the vase life of cut flowers was evaluated in comparison with a prior art formulation in a series of experiments described in Examples 6–9 below.

EXAMPLE 6

'White Sim' standard carnations were purchased from a local supermarket. Each flower stem was re-cut under water and then placed into an aqueous treatment solution at a concentration of 10 g/liter of either: (a) a prior art glucose-based cut flower preservative which did not contain an ACC synthase activity inhibitor (Example 3) or (b) a complete glucose-based cut flower preservative in accordance with the present invention containing 0.58 parts by weight AVG (Example 4). All "holding" solutions were made with distilled water. Six flowers (3 flowers in each of 2 bottles) were used for each treatment. Solution volumes were maintained daily with distilled water. All flowers were placed on a laboratory bench under constant illumination and a temperature of approximately 22° C. Petal in-rolling was used as the criterion for non-viability. The results of this test appear in Table 2.

TABLE 2

| Days in Solution | Percent Viable Flowers Remaining Prior Art Glucose-Based Formulation | Percent Viable Flowers Remaining Glucose-AVG-Based Formulation |
|---|---|---|
| 4 | 50 | 100 |
| 5 | 50 | 100 |
| 6 | 33 | 100 |
| 7 | 33 | 100 |
| 8 | 17 | 100 |
| 9 | 17 | 100 |
| 10 | 0 | 100 |
| 11 | 0 | 66 |
| 12 | 0 | 66 |
| 13 | 0 | 33 |
| 14 | 0 | 33 |

EXAMPLE 7

Freshly harvested 'White Sim' standard carnations, grown and handled according to accepted commercial practices (however, not "pulse" treated with silver thiosulfate, STS) were used. These flowers were purchased from a Denver, CO grower and shipped via overnight air express to Chicago. Upon arrival, each flower stem was re-cut under water and then placed into an aqueous treatment solution at a concentration of 10 g/liter of either: (a) complete glucose-based prior art cut flower preservative (Example 3), (b) complete glucose-based cut flower preservative containing 0.58 parts by weight AVG (Example 4), or (c) complete glucose-based cut flower preservative containing 0.50 parts by weight AOAA (Example 5). All "holding" solutions were made with distilled water. Six flowers (3 flowers in each of 2 bottles) were used for each treatment. Solution volumes were maintained daily with distilled water. All flowers were placed on a laboratory bench under constant illumination and a temperature of approximately 22° C. Petal in-rolling was used as the criterion for non-viability. The results appear in Table 3.

TABLE 3

| Days In Solution | Percent Viable Flowers Remaining Glucose Based Formulation | Percent Viable Flowers Remaining Glucose-Based AVG Formulation | Percent Viable Flowers Remaining Glucose-Based AOAA Formulation |
|---|---|---|---|
| 4 | 100 | 100 | 100 |
| 5 | 63 | 100 | 100 |
| 6 | 17 | 100 | 100 |
| 7 | 0 | 100 | 100 |
| 8 | 0 | 83 | 83 |
| 9 | 0 | 67 | 67 |
| 10 | 0 | 50 | 33 |
| 11 | 0 | 50 | 17 |
| 12 | 0 | 33 | 17 |
| 13 | 0 | 33 | 0 |
| 14 | 0 | 17 | 0 |
| 15 | 0 | 0 | 0 |

EXAMPLE 8

Freshly harvested 'White Sim' standard carnations, grown and handled according to accepted commercial practices (however not "pulse" treated with silver thiosulfate, STS) were used. These flowers were purchased from a Denver, Colo. grower and shipped via overnight air express to Chicago. Upon arrival, each flower stem was re-cut under water and then placed into and aqueous treatment solution of (a) 0.50 parts by weight AVG only, or aqueous treatment solutions at a concentration of 10 g/liter of either: (b) complete glucose-based cut flower preservative according to the prior art (Example 3), or (c) complete glucose-based cut flower preservative containing 0.58 parts by weight AVG (Example 4). All "holding" solutions were made with distilled water. Twenty-four flowers (3 flowers in each of 8 bottles) were used for each treatment. Solution volumes were maintained daily with distilled water. All flowers were placed on a laboratory bench under constant illumination and a temperature of approximately 22° C. Petal in-rolling was used as the criterion for non-viability. The results are presented in Table 4.

TABLE 4

| Days In Solution | Percent Viable Flowers Remaining Glucose Based Formulation | Percent Viable Flowers Remaining AVG-Only | Percent Viable Flowers Remaining Glucose-Based AVG Formulation |
|---|---|---|---|
| 5 | 100 | 100 | 100 |
| 6 | 96 | 100 | 100 |
| 7 | 79 | 100 | 100 |
| 8 | 38 | 42 | 100 |
| 9 | 0 | 17 | 100 |
| 10 | 0 | 17 | 92 |
| 11 | 0 | 8 | 71 |
| 12 | 0 | 0 | 38 |
| 13 | 0 | 0 | 17 |
| 14 | 0 | 0 | 4 |

EXAMPLE 9

Freshly harvested flowers, grown and handled according to accepted commercial practices were used. The flowers were purchased from commercial growers and shipped via overnight air express to Chicago. Upon arrival, each flower stem was re-cut under water and then placed into an aqueous treatment solution prepared from aformulation described in either (a) Example 1 (prepared at a concentration of 20 grams/liter), (b) Example 2 (prepared at a concentration of 10 grams/liter), or (c) Example 3 (prepared at a concentration of 10 grams/liter). All "holding" solutions were made with a municipal tap water supply. Fifteen flowers (5 flowers in each of 3 bottles) were used for each treatment. Solution volumes were replenished or refilled with freshly prepared solution as needed. All flowers were placed on a laboratory bench under constant illumination and a temperature of approximately 22° C. The flowers were evaluated visually on a daily basis for viability. The results are presented in Table 5.

TABLE 5

| Flower Type | Example 1 (Average Vase Life in Days) | Example 2 (Average Vase Life in Days) | Example 3 (Prior Art) (Average Life in Days) |
|---|---|---|---|
| White Sim Carnations (Not Previously Treated with Silver Thiosulfate) | 18 | 25 | 9 |
| White Sim Carnations (Previously Treated with Silver Thiosulfate) | 19 | 21 | 22 |
| Bouvardia | 17 | 22 | 21 |
| Rosaria Alstroemeria | 23 | 24 | 17 |
| Madame DelBard Roses | 14 | 12 | 14 |

TABLE 5-continued

| Flower Type | Example 1 (Average Vase Life in Days) | Example 2 (Average Vase Life in Days) | Example 3 (Prior Art) (Average Life in Days) |
|---|---|---|---|
| Blue Diamond Iris | 6 | 6 | 6 |
| Dutch Master Daffodils | 11 | 10 | 9 |
| Prominence Tulips | 6 | 6 | 6 |

The foregoing examples are illustrative of the present invention and should not be read as limiting the scope of the invention as it is defined by the appended claims.

We claim:

1. A solid cut flower preservative formulation characterized by extended shelf life comprising
   (a) from about 1 part by weight to about 99 parts by weight of a sugar, glycoside or mixture thereof,
   (b) from about 0.05 part by weight to about 2 part by weight of an ACC synthase inhibitor selected from L-trans-2-amino-4-(2-aminoethoxy)-3-butenoic acid and carboxymethoxylamine,
   c) from about 0.5 part by weight to about 8 parts by weight of aluminum sulfate having between about 21 and about 27 percent by weight water of hydration, and
   (d) from about 0.05 part by weight to about 5 parts by weight of an antimicrobial agent.

2. A solid cut flower preservative formulation as defined by claim 1 further comprising from about 0.1 part by weight to about 5 parts by weight sodium or potassium chloride, from about 0.01 parts by weight to about 2 parts by weight of a nonionic or anionic surfactant.

3. A solid cut flower preservative formulation as defined by claim 2 wherein said ACC synthase inhibitor is L-trans-2-amino-4-(2-aminoethoxy)-3-butenoic acid.

4. A solid cut flower preservative formulation as defined by claim 2 wherein said ACC synthase inhibitor carboxymethoxylamine.

5. A solid cut flower preservative formulation as defined by claim 1 wherein said sugar is selected from the group consisting of ribose, arabinose, xylose lyxose, allose, altrose, glucose, mannose, gulose, idose, galactose, talose, fructose, alkyl-α-glycosides, alkyl-β-glycosides, aryl-αglucosides, aryl-β-glycosides, lactose, maltose, cellobiose, gentiobiose, turanose, iso-maltose, laminaribose, melibiose, sucrose, trehalose, raffinose and gentianose.

6. A solid cut flower preservative formulation as defined by claim 5 wherein said sugar is sucrose.

7. A solid cut flower preservative formulation comprising
   (a) from about 80 part by weight to about 99 parts by weight of a sugar, glycoside, or mixture thereof,
   (b) from about 0.2 part by weight to about 1 part by weight of an ACC synthase inhibitor selected from L-trans-2-amino-4-(2-aminoethoxy)-3-butenoic acid and carboxymethoxylamine,
   c) from about 1 part by weight to about 5 parts by weight of aluminum sulfate having between about 21 and about 27 percent by weight water of hydration, and
   (d) from about 0.2 part by weight to about 2 parts by weight of an antimicrobial agent.

8. A solid cut flower preservative formulation as defined by claim 1 wherein said aluminum sulfate contains between about 21 and about 24 weight percent water of hydration.

* * * * *